United States Patent [19]

Harris et al.

[11] 4,396,616

[45] Aug. 2, 1983

[54] SUBSTITUTED ENANTHOLACTAM DERIVATIVES AS ANTIHYPERTENSIVES

[75] Inventors: Elbert E. Harris, Westfield; David Taub, Metuchen; Eugene D. Thorsett, Fanwood, all of N.J.

[73] Assignee: Merck & Co., Inc., Rahway, N.J.

[21] Appl. No.: 299,051

[22] Filed: Sep. 4, 1981

[51] Int. Cl.$^3$ .................. A61K 31/395; A61K 31/40; C07D 225/02; C07D 487/08
[52] U.S. Cl. .................................... 424/244; 424/274; 260/239.3 R
[58] Field of Search ................. 260/239.3 R; 424/244, 424/274

[56] References Cited

U.S. PATENT DOCUMENTS 4,221,789  9/1980  Rodriguez et al. .......... 260/239.3 R Primary Examiner—Robert T. Bond
Attorney, Agent, or Firm—Salvatore C. Mitri; Rudolph J. Anderson, Jr.

[57] ABSTRACT

Substituted enantholactam dipeptides and derivatives thereof are disclosed which are useful as converting enzyme inhibitors and as antihypertensives.

18 Claims, No Drawings

SUBSTITUTED ENANTHOLACTAM DERIVATIVES AS ANTIHYPERTENSIVES

BACKGROUND OF THE INVENTION

This is a continuation-in-part application of application Ser. No. 194,691 filed Oct. 6, 1980, now abandoned.

The invention in its broad aspects relates to enantholactam dipeptides and derivatives thereof which are useful as converting enzyme inhibitors and as antihypertensives. The compounds of this invention can be shown by the following formula:

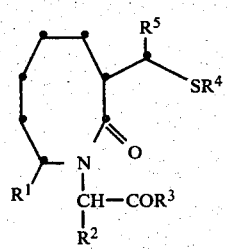

In which
R$^1$ is hydrogen, loweralkyl, cycloalkyl, aminoalkyl, hydroxyalkyl, aryl, heteroaryl, aralkyl, heteroaralkyl, heterocycloalkyl, or substituted aryl wherein the substituent is halo, alkyl, aminoalkyl or alkoxy;
R$^2$ is hydrogen, lower alkyl, aminoloweralkyl, indolyl lower alkyl or phenyl lower alkyl;
R$^3$ is hydroxy, lower alkoxy or aralkyloxy;
R$^4$ is hydrogen or lower alkanoyl;
R$^5$ is hydrogen or lower alkyl;
and, the pharmaceutically acceptable salts thereof.

Preferred are compounds of Formula I wherein
R$^1$ is hydrogen or lower alkyl;
R$^2$ is hydrogen or lower alkyl;
R$^3$ is hydroxy or lower alkoxy;
R$^4$ is hydrogen or lowe alkanoyl; and,
R$^5$ is hydrogen.

The preferred compounds of this invention also include the pharmaceutically acceptable salts thereof.

The products of Formula (I) and the preferred subgroups can be produced by one or more of the methods and subroutes depicted in the following Flow Sheets. The definitions of R$^1$, R$^2$, R$^3$, R and R$^5$ are the same as in Formula (I) except where noted.

Method A

An enantholactam derivative II is reacted with an iodoester III in a suitable solvent such as THF or DMF in the presence of a strong base like sodium hydride to afford IV. Reaction of IV with a strong base such as lithium diisopropylamide in a solvent like THF followed by treatment with an aldehyde V gives the alcohol VI. Dehydration of the alcohol through the agency of a suitable ester and a strong base, for example, the methanesulfonate and an amidine type base, gives the olefin VII. Treatment of this olefin with a mercapto compound VIII such as thioacetic acid gives I.

Groups R$^3$ and R$^4$ may be modified by known methods, if desired. For example, if R$^3$=OCH$_3$ and R$^4$=CH$_3$CO, the diester I can be converted to the mercapto acid (R$_3$=OH, R$_4$=H) by basic hydrolysis. Alternatively, if for I R$^3$=O-t-Bu and R$^4$=CH$_3$CO, the S-acetyl carboxylic acid (R$^3$=OH, R$^4$=CH$_3$CO) can be obtained by mild acid hydrolysis of I with, for example, trifluoroacetic acid.

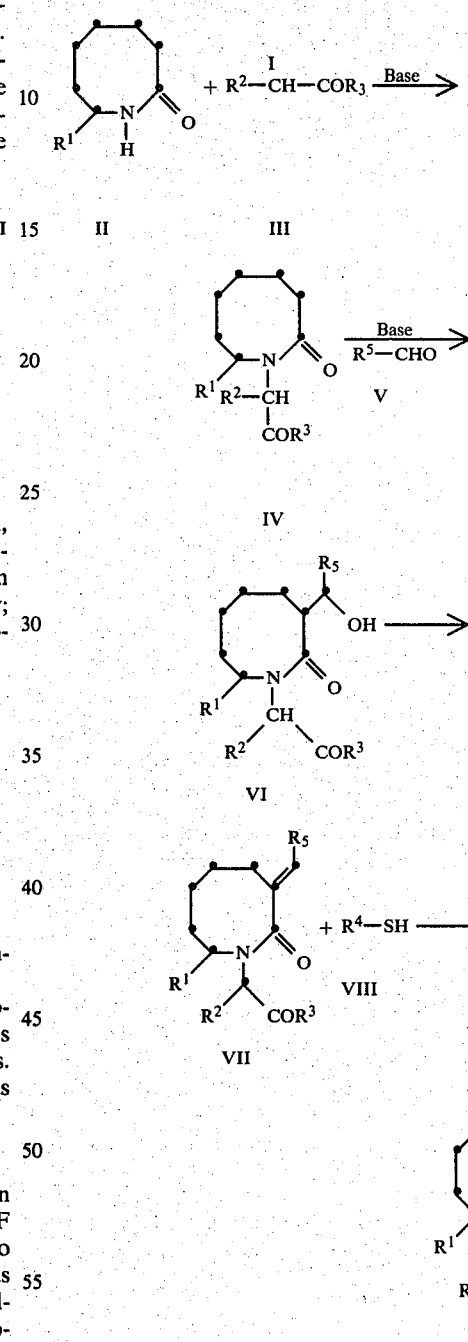

FLOW SHEET I

METHOD B

A bromoenantholactam derivative IX [prepared according to H. Nagasawa, et al., *J. Med. Chem.*, 14, 501 (1971)] is reacted with an iodoester III as described in Method A to afford X. The monohalide X can be reacted with a suitable trivalent phosphorus compound, such as triphenylphosphine, followed by a base like sodium hydroxide, analogous to a procedure described by G. Howie, et al. [*J. Med. Chem.*, 17 840 (1974)]. The resulting XI is then reacted with an aldehyde V to afford olefin VII which can be converted to I as described in Method A above.

FLOW SHEET II

METHOD B:

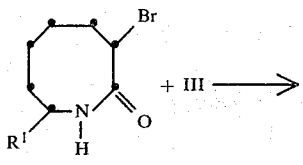

IX

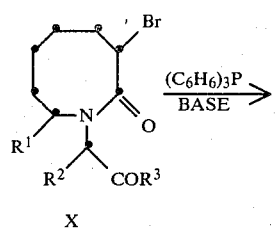

X

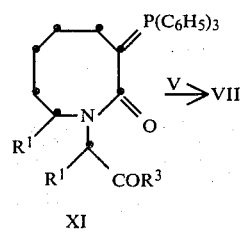

XI

The starting materials which are required for the above processes herein described are known in the literature or can be made by known methods from known starting materials.

In products of general Formula (I), the carbon atoms to which, $R^1$, $R^2$ and $R^5$ are attached and the ring carbon atom to which the fragment

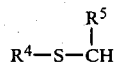

is attached may be asymmetric. The compounds accordingly exist in diastereoisomeric forms or in mixtures thereof. The above described syntheses can utilize racemates, enantiomers or diastereomers as starting materials. When diastereomeric products result from the synthetic procedures, the diastereomeric products can be separated by conventional chromatographic of fractional crystallization methods. When racemic products result, they may be resolved by crystallization of salts of optically active acids or bases or by other methods known in the art. In general, the part-structures, i.e.,

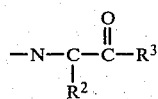

of Formula (I) can be in two configurations (S or R) and both are herein covered.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like. Also salts with organic and inorganic acids may be prepared, which are preferred, e.g., HCl, HBr, $H_2SO_4$, $H_3PO_4$, methanesulfonic, toluenesulfonic, maleic, fumaric, camphorsulfonic. The non-toxic physiologically acceptable salts are particularly valuable, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotension converting enzyme are effective antihypertensive agents in a variety of animal models and are useful clinically, for example, in many human patients with renovascular, malignant and essential hypertension. See, for example, D. W. Cushman et al., *Biochemistry* 16 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206 136 (1970) in which the hydrolysis of carbobenzyloxyphenylalanylhistidinylleucine is measured. In vivo evaluations may be made, for examle, in normotensive rats challenged with angiotensin I by the technique of J. R. Weeks and J. A. Jones, *Proc. Soc. Exp. Biol. Med.,* 104 646 (1960) or in a high renin rat model such as that of S. Koletsky et al., *Proc. Soc. Exp. Biol. Med.,* 125 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage that will at least be pharmaceutically active. Although the dose will vary depending on severity of disease, weight of patient and other factors which a person skilled in the art will recognize, the dosage range will be about 10 to 500 mg. per patient which can be given several times a day.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like as well, as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of the invention effective clinically in the 10–1000 mg per day range can be effectively combined at levels at the 2–1000 mg per day range with the following compounds at the indicated per day dose range: hydrochlorothiazide (10–100 mg), timolol (5–60 mg), methyl dopa (65–2000 mg), the pivaloyloxyethyl ester of methyl dopa (30–1000 mg), indacrinone and variable ratios of its enantiomers (25–150 mg) and (+)-4-{3-{[2-(1-hydroxycyclohexyl)ethyl]-4-oxo-2-thiazolidinyl}-propyl}benzoic acid (10–100 mg).

In addition, the triple drug combinations of hydrochlorothiazide (10–100 mg) plus timolol (5–60 mg) plus converting enzyme inhibitor of this invention (2–1000 mg) or hydrochlorothiazide (10–100 mg) plus amiloride (5–20 mg) plus converting enzyme inhibitor of this invention (2–1000 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, the compounds shown above are formulated into pharmaceutical compositions as discussed below.

About 10 to 500 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. As mentioned earlier, the preferred diastereomers of these examples can be readily isolated by conventional column chromatography or fractional crystallization.

EXAMPLE 1

1-(1-Carboxyethyl)-3-mercaptomethylperhydroazocin-2-one

Remove the oil from 1.35 g of 50% sodium hydride oil dispersion and suspend the hydride in 25 ml THF. Add to this stirred suspension a premixed solution of 3.40 g perhydroazocin-2-one and 6.38 g ethyl 2-iodopropionate and continue stirring at ambient temperature for 3.5 hours. Quench the reaction with 30 ml 10% $NH_4Cl$ solution. Remove the THF at aspirator pressure and extract the mixture with ether. Wash the combined ether extracts with dilute sodium thiosulfate solution, water and brine, then dry over $Na_2SO_4$. Filter and concentrate the filtrate to obtain 4.04 g of 1-(1-ethoxycarbonylethyl)perhydroazocin-2-one.

Dissolve 90 mg of this ester in 0.5 ml ethanol and add 1 ml 1.0 N NaOH. Stir the mixture at room temperature for 3 hours, then dilute with water and extract with ether. Add solid sodium dihydrogen phosphate to the aqueous phase until it is acidic, then extract with ethyl acetate. Dry the ethyl acetate over $Na_2SO_4$, filter and concentrate to obtain 1-(1-carboxyethyl)perhydroazocin-2-one, m.p. 166–167 (from acetone-ether).

Prepare a solution of lithium diisopropylamide from 660 mg diisopropylamine in 5 ml THF and 3.75 ml 1.6 M n-butyl lithium in hexane at −78°. Add 600 mg of the lactam acid dissolved in 10 ml THF over 5 min. Warm the resulting solution to −20° and maintain for 1 hour. Bubble gaseous formaldehyde into solution over a period of 2 hours. Add 15 ml 10% $NH_4Cl$ solution and remove the THF in vacuo. Saturate the remaining aqueous phase with sodium dihydrogen phosphate and extract with ethyl acetate. Dry ($Na_2SO_4$) and concentrate the extracts to obtain crude 1-(1-carboxyethyl)-3-hydroxymethylperhydroazocin-2-one. Convert this acid to the methyl ester with ethereal diazomethane and purify by silica gel chromatography eluting with acetonechloroform (35:65) to obtain pure 1-(1-methoxycarbonylethyl)-3-hydroxymethylperhydroazocin-2-one; tlc: acetone:chloroform (35:65); $R_f$ 0.4.

Chill a solution of 105 mg of this hydroxy ester in 0.5 ml benzene and 0.5 ml pyridine to 0° and add a mixture of 0.2 ml methansulfonyl chloride in 1 ml pyridine. Store the mixture at 0° overnight then add to cold 10%

NH₄Cl solution. Extract with ethyl acetate and wash the extracts with cold 1 N HCl and brine. Dry (Na$_2$SO$_4$) and decolorize the ethyl acetate solution with charcoal. Filter and concentrate to obtain 1-(1-methoxycarbonylethyl)-3-methanesulfonyloxymethylperhydroazocin-2-one; tlc: acetone:chloroform (35:65); $R_f$ 0.70.

Dissolve 105 mg of this ester and 0.2 ml 1.8-diazabicyclo (5.4.0)undec-7-ene in 1.5 ml benzene and store the solution at 80°–85° for 20 hours. Cool the reaction, add it to cold aqueous sodium dihydrogen phosphate, and extract with ethyl acetate. Dry (Na$_2$SO$_4$) and concentrate the extract to obtain 1-(1-methoxycarbonylethyl)-3-methyleneperhydroazocin-2-one; tlc: acetone:chloroform (1:9); $R_f$ 0.54.

IR (CHCl$_3$, cm$^{-1}$): 1735, 1620, 1430, 980, 920.

NMR (CDCl$_3$): $\delta$1.46 (d, J=7, 3H); $\delta$3.70 (s, 3H); $\delta$4.65 (q, J=7, 2H); $\delta$4.97, 5.07 (CH$_2$=).

Dissolve 200 mg of this ester in 5 ml thiolacetic acid and store the solution at room temperature overnight. Concentrate the reaction and flush with benzene in vacuo. Purify the 1-(1-methoxycarbonylethyl)-3-acetylmercaptomethylperhydroazocin-2-one by silica gel chromatography.

Hydrolyze 200 mg of this diester under an atmosphere of nitrogen in methanolic sodium hydroxide. Acidify the hydrolysate to pH 2 and extract with ethyl acetate. Dry and concentrate the extracts to obtain 1-(1-carboxyethyl)-3-mercaptomethylperhydroazocin-2-one.

Similarly, prepare 1-carboxymethyl-3-mercaptomethylperhydroazocin-2-one using ethyl iodoacetate in place of ethyl iodopropionate.

EXAMPLE 2

1-Carboxymethyl-3-mercaptomethylperhydroazocin-2-one

To a vigorously stirred suspension of 0.55 g sodium hydride in 30 ml tetrahydrofuran add over 20 min. a solution of 5.0 g t-butyl iodoacetate and 4.12 g 3-bromoperhydroazocin-2-one [Nagasawa et al., *J. Med. Chem.*, 14 501 (1971)] dissolved in 35 ml tetrahydrofuran. After the addition is completed stir the reaction at room temperature for 1.5 hours then quench by the addition of 5–6 ml of saturated NH₄Cl solution. Filter the reaction and concentrate the filtrate. Add ether to the residue, filter and wash the filtrate with H₂O and brine. Dry the ether solution and concentrate to obtain 1-t-butoxycarbonylmethyl-3-bromoperhydroazocin-2-one. Prepare an analytical sample by silica gel chromatography. M.p. 107.5–109. Anal. (C$_{13}$H$_{22}$BrNO$_3$). Calc: C, 48.75; H, 6.93; N, 4.37. Found: C, 48.78; H, 7.12; N, 4.26.

Reflux a solution of 3.19 g of this halide with 2.62 g triphenylphosphine in 50 ml THF. Isolate the crude phosphonium salt, suspend it in H₂O and add dropwise 10% NaOH. Extract the mixture with chloroform, concentrate the extracts and isolate the desired ylide.

Reflux a suspension of 2.4 g of this ylid and 0.3 g paraformaldehyde in 75 ml THF under a nitrogen atmosphere. After 3 hours, cool the reaction and reduce the volume in vacuo. Add petroleum ether and pass the solution through a short silica gel column. Remove the solvent and isolate 1-t-butoxycarbonylmethyl-3-methyleneperhydroazocin-2-one.

Convert this compound to the desired mercapto acid as described in Example 1.

EXAMPLE 3

1-(1-Carboxyethyl)-3-acetylthiomethylperhydroazocin-2-one

Hydrolyze 100 mg 1-(1-ethoxycarbonylethyl)-3-methyleneperhydroazocin-2-one, prepared in Example 1, with dilute sodium hydroxide. Carefully acidify the hydrolysate to pH 2 and extract with ethyl acetate. Dry and concentrate to obtain 1-(1-carboxyethyl)-3-methyleneperhydroazocin-2-one.

Treat this acid with 5 ml thiolacetic acid as described in Example 1 and isolate 1-(1-carboxyethyl)-3-acetylthiomethylperhydroazocin-2-one as a mixture of diastereomers.

Separate the diastereomers by reverse phase chromatography using acetonitrile water solvent.

EXAMPLE 4

1-Carboxymethyl-3-acetylthiomethylperhydroazocin-2-one

Hydrolyze 100 mg 1-ethoxycarbonylmethyl-3-methyleneperhydroazocin-2-one (prepared as in Example 1) with base as described in Example 3. Treat the resulting 1-carboxymethyl-3-methyleneperhydroazocin-2-one with thiolacetic acid as described in Example 3 and isolate the desired 1-carboxymethyl-3-acetylthiomethylperhydroazocin-2-one.

Alternatively, prepare the 1-carboxymethyl-3-methyleneperhydroazocin-2-one by treatment of 150 mg 1-t-butoxycarbonylmethyl-3-methyleneperhydroazocin-2-one (prepared as in Example 2) with 5 ml trifluoroacetic acid.

EXAMPLE 5

1-(1-Carbomethoxyethyl)-3-acetylthiomethylperhydroazocin-2-one

A solution of 50 mg of 1-(1-carbomethoxyethyl)-3-methyleneperhydroazocin-2-one in thioacetic acid (0.5 ml) is kept at room temperature for 18 hours. Toluene (5 ml) is added and the mixture is concentrated to dryness under reduced pressure. The product is purified by preparative tlc on silica gel (system 5% acetone in chloroform) to yield the title compound (62 mg) as a colorless oil.

TLC 5% acetone CHCl$_3$ $R_f$=0.4; i.r. (CHCl$_3$) 1735, 1680, 1635 cm$^{-1}$; m.s. 301 (M), 258 (M-43), 242 (M-59), 266 (M-75).

EXAMPLE 6

1-(1-Carboxyethyl)-3-thiomethylperhydroazocin-2-one

To a solution of 60 mg of 1-(1-methoxycarbonylethyl)-3-acetylthiomethylperhydroazocin-2-one in methanol (0.4 ml) under nitrogen is added 0.8 ml of 1.0 N aqueous sodium hydroxide under nitrogen. The mixture is stirred three hours at room temperature, and it is then acidified by adding to 15 ml of saturated aqueous sodium dihydroxen phosphate. Extraction with ethyl acetate, drying over sodium sulfate and evaporation of solvent under reduced pressure yields the title compound (45 mg) as a colorless gum:

TLC (silic gel)-system ethylacetate:acetone:acetic acid=90:10:1 $R_f$=0.6; i.r. (chf) 3350-2900, 1710, 1625 cm$^{-1}$; m.s. 245 (M), 212 (M-33).

EXAMPLE 7

8-Substituted 1-carboxymethyl-3-mercaptomethylperhydroazocin-2-ones of Formula I ($R^1 \neq H$)

Alkylation of the lactams listed in Table I with t-butyl iodoacetate as described in Example 2 affords the corresponding 1-t-butoxycarbonylmethylperhydroazocin-2-ones ($R^1 \neq H$). After removal of the t-butyl ester with anhydrous trifluoracetic acid, the resulting 1-carboxymethylperhydroazocin-2-ones are reacted with formaldehyde in the presence of lithium diisopropylamide as described in Example 1. Following the procedure of this example, the alcohol products are purified and converted to the corresponding 1-methoxycarbonylmethyl-3-methyleneperhydroazocin-2-ones.

Reaction of these olefinic lactams with thiolacetic acid as described in Example 1 affords 8-substituted-1-methoxycarbonylmethyl-3-acetylmercaptomethylperhydroazocin-2-ones. Basic hydrolysis of these esters as described affords the compounds of Formula I wherein $R^2$, $R^4$ and $R^5=H$, $R^3=OH$ and $R^1$ is as listed in Table I.

EXAMPLE 8

8-Substituted-1-carboxymethyl-3-acetylmercaptomethylperhydroazocin-2-ones of Formula I Basic hydrolysis of the 8-substituted-1-methoxycarbonylmethyl-3-methyleneperhydroazocin-2-ones (Example 7) as described in Example 3 affords 8-substituted-1-carboxymethyl-3-methyleneperhydroazocin-2-ones. Reaction of these lactams with thiolacetic acid as described in Example 3 affords the compounds of Formula I wherein $R^2$ and $R^5=H$, $R^3=OH$, $R^4=$acetyl and $R^1$ is as described in Table I.

Alternatively, these compounds may be obtained by reacting the 8-substituted-1-carboxymethyl-3-mercaptomethylperhydroazocin-2-ones described in Example 7 with acetic anhydride or acetyl chloride in the presence of pyridine.

TABLE I

| 8-Substituted Enantholactams | |
|---|---|
| | $R^1$ |
| a. | methyl |
| b. | ethyl |
| c. | n-propyl |
| d. | cyclohexyl |

EXAMPLE 9

8-(2-Aminoethyl)-1-carboxymethyl-3-mercaptomethylperhydroazocin-2-one 8-(2-Aminoethyl)perhydroazocin-2-one may be converted to the N-phthalimidyl derivative and then brominated using the procedure of Nagasawa et al. [*J. Med. Chem.*, 14, 501 (1971)]. Alkylation of this lactam with t-butyl iodoacetate as described in Example 2 will afford 3-bromo-1-t-butoxycarbonylmethyl-8-(2-phthalimidylethyl)perhydroazocin-2-one. Reaction of this halide with triphenylphosphine will afford a phosphonium salt which, after treatment with triethylamine will afford an ylid. Reaction of this ylid with paraformaldehyde as described in Example 2 will afford 1-t-butoxycarbonylmethyl-3-methylene-8-(2-phthalimidylethyl)perhydroazocin-2-one. Treatment of this compound with thiolacetic acid followed by sequential treatment with anhydrous trifluoracetic acid to remove the t-butylester and then hydrazine to cleave the phthalimidyl and thioacetate functions would afford the desired product.

EXAMPLE 10

A typical tablet contains 1-(1-carboxyethyl)-3-mercaptomethylperhydroazocin-2-one (25 mg.), pregelatinized starch USP (82 mg.), microcrystalline cellulose (82 mg.) and magnesium stearate (1 mg.).

EXAMPLE 11

Compressed Tablet containing 50 mg. of active ingredient

| | Per tablet, Mg. |
|---|---|
| 1-(1-Carboxyethyl)-3-mercaptomethyl-perhydroazocin-2-one | 50 |
| Calcium phosphate dibasic | 245 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions

Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

EXAMPLE 12

Dry filled capsule containing 5 mg. of active ingredient.

| | Per capsule, mg. |
|---|---|
| 1-(1-Carboxyethyl)-3-mercaptomethylperhydroazocin-2-one | 5 |
| Lactose | 273 |
| Magnesium stearate | 2 |
| Mixed powders | 280 |

Mix the active ingredient above, lactose, and magnesium stearate and reduce to a No. 60 mesh powder. Encapsulate, filling 280 mg. in each No. 2 capsule.

The above formulations can be employed to prepare compressed tablets or capsules of other novel compounds of this invention hereinbefore described.

While the above examples describe the preparation of certain compounds which are illustrative of the novel compounds of this invention and certain specific dosage forms suitable for administering the novel compounds, it is to be understood that the invention is not to be limited to the specific compounds described in the examples or by the specific reaction conditions described for the preparation of these compounds or by the specific ingredients included in the pharmaceutical preparations, but is to be understood to embrace variations and modifications thereof.

What is claimed is:

1. A compound of the formula:

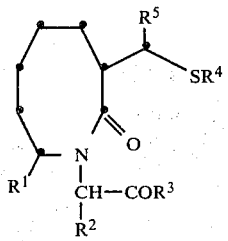

in which
R$^1$ is hydrogen, lower alkyl, cycloloweralkyl having 3 to 7 ring C atoms, aminoloweralkyl, hydroxyloweralkyl, or substituted aryl wherein the substituent is halo, loweralkyl, aminoloweralkyl or loweralkoxy;
R$^2$ is hydrogen, lower alkyl, aminolower alkyl, indolyl lower alkyl or phenyl lower alkyl;
R$^3$ is hydroxy, or lower alkoxy;
R$^4$ is hydrogen or lower alkanoyl;
R$^5$ is hydrogen or lower alkyl; and,
the pharmaceutically acceptable salts thereof.

2. The compound of claim 1 wherein
R$^1$ is hydrogen or lower alkyl;
R$^2$ is hydrogen or lower alkyl;
R$^3$ is hydroxy or lower alkoxy;
R$^4$ is hydrogen or lower alkanoyl; and,
R$^5$ is hydrogen.

3. The compound of claim 2 which is 1-(1-carboxyethyl)-3-mercaptomethylperhydroazocin-2-one.

4. The compound of claim 2 which is 1-(1-methoxycarbonyl)-3-acetylthiomethylperhydroazocin-2-one.

5. A method of treating hypertension which comprises administering to a patient in need of such treatment an antihypertensively effective amount of a compound of the formula:

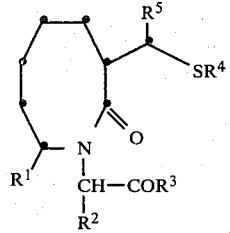

in which
R$^1$ is hydrogen, lower alkyl, cycloloweralkyl having 3 to 7 ring C atoms, aminoloweralkyl, hydroxyloweralkyl, or substituted aryl wherein the substituent is halo, loweralkyl, aminoloweralkyl, or loweralkoxy;
R$^2$ is hydrogen, lower alkyl, amino lower alkyl indolyl lower alkyl or phenyl lower alkyl;
R$^3$ is hydroxy, or lower alkoxy;
R$^4$ is hydrogen or lower alkanoyl;
R$^5$ is hydrogen or lower alkyl; and,
the pharmaceutically acceptable salts thereof.

6. The method of claim 5 wherein
R$^1$ is hydrogen or lower alkyl;
R$^2$ is hydrogen or alkyl;
R$^3$ is hydroxy or lower alkoxy;
R$^4$ is hydrogen or lower alkanoyl; and,
R$^5$ is hydrogen.

7. The method of claim 6 wherein said compound is 1-(1-carboxyethyl)-3-mercaptomethylperhydroazocin-2-one.

8. The method of claim 6 wherein said compound is 1-(1-methoxycarbonyl)-3-acetylthiomethylperhydroazocin-2-one.

9. A pharmaceutical composition useful in the treatment of hypertension which comprises a pharmaceutically acceptable carrier and an antihypertensively effective amount of a compound of the formula:

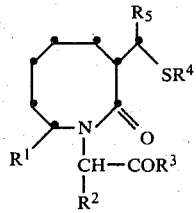

in which
R$^1$ is hydrogen, lower alkyl, cycloloweralkyl having 3 to 7 ring C atoms, aminoloweralkyl, hydroxyloweralkyl, or substituted aryl wherein the substituent is halo, loweralkyl, aminoloweralkyl, or loweralkoxy;
R$^2$ is hydrogen, lower alkyl, amino lower alkyl, indolyl lower alkyl or phenyl lower alkyl;
R$^3$ is hydroxy, or lower alkoxy;
R$^4$ is hydrogen or lower alkanoyl;
R$^5$ is hydrogen or lower alkyl;
and the pharmaceutically acceptable salts thereof.

10. The composition of claim 9 wherein said compound is 1-(1-carboxyethyl)-3-mercaptomethylperhydroazocin-2-one.

11. The composition of claim 9 wherein said compound is 1-(1-methoxycarbonyl)-3-acetylthiomethylperhydroazocin-2-one.

12. A pharmaceutical composition useful in the treatment of hypertension which comprises a pharmaceutically acceptable carrier; an antihypertensively effective amount of a compound of the formula:

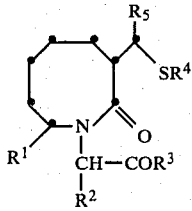

in which
R$^1$ is hydrogen, lower alkyl, cycloloweralkyl having 3 to 7 ring C atoms, aminoloweralkyl, hydroxyloweralkyl, arloweralkyl, or substituted aryl wherein the substituent is halo, loweralkyl, aminoloweralkyl, or loweralkoxy;
R$^2$ is hydrogen, lower alkyl, amino lower alkyl, indolyl lower alkyl or phenyl lower alkyl;
R$^3$ is hydroxy, or lower alkoxy;
R$^4$ is hydrogen or lower alkanoyl;
R$^5$ is hydrogen or lower alkyl;
the pharmaceutically acceptable salts thereof; and, an antihypertensive and/or diuretic compound selected from the group consisting of amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, hydroflumethiazide, metalazone, metoprololtartrate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, rifetipine, verapamil, diltiazam, flumethiazide, bendroflumethiazide, atenolol, (+)-4-{3-{[2-(1-hydroxycyclohexyl)ethyl]-4-oxo-2-thiazolidinyl}propyl}benzoic acid, bumetanide, prazosin, propranolol, *rauwolfia serpentina*, rescinnamine, reserpine, spironolactone, timolol, trichlormethiazide, benzthiazide, guinethazone, triamterene, acetazolamide, aminophylline, cyclothiazide, merethoxylline procaine, as well as admixtures and combinations thereof.

13. The composition of claim 12 wherein said antihypertensively effective compound is 1-(1-carboxyethyl)-3-mercaptomethylperhydroazocin-2-one.

14. The composition of claim 12 wherein said antihypertensively effective compound is 1-(1-methoxycarbonyl)-3-acetylthiomethylperhydroazocin-2-one.

15. A process for preparing compounds of the formula:

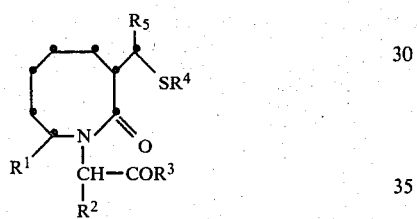

wherein:
R$^1$ is hydrogen, lower alkyl, cycloloweralkyl having 3 to 7 ring C atoms, aminoloweralkyl, hydroxyloweralkyl, arloweralkyl, or substituted aryl wherein the substituent is halo, loweralkyl, aminoloweralkyl, or loweralkoxy;
R$^2$ is hydrogen, lower alkyl, amino lower alkyl, indolyl lower alkyl, or phenyl lower alkyl;
R$^3$ is hydroxy, or lower alkoxy;
R$^4$ is hydrogen or lowr alkanoyl; and,
R$^5$ is hydrogen or lower alkyl; which process comprises treating a compound of the formula

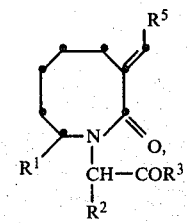

with R$^4$-SH wherein R$^1$, R$^2$, R$^3$, R$^4$ and R$^5$ are as defined above, followed by removal of acyl and ester groups, if necessary, to yield the desired product and, if desired, isolating the biologically more active isomer by chromatography, fractional crystallization, or by resolution with an appropriate, optically active base and, if desired, preparing a salt of the desired product by conventional means.

16. The process of claim 15 wherein:
R$^1$ is hydrogen or lower alkyl;
R$^2$ is hydrogen or lower alkyl;
R$^3$ is hydroxy or lower alkoxy;
R$^4$ is hydrogen or lower alkanoyl; and,
R$^5$ is hydrogen.

17. The compound:

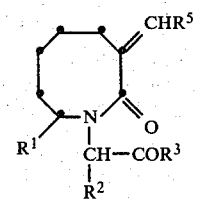

wherein R$^1$, R$^2$, R$^3$, and R$^5$ are as defined in claim 1.

18. The compound:

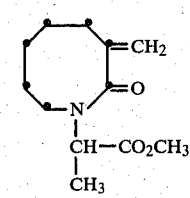

and the corresponding carboxylic acid thereof.

* * * * *